(12) United States Patent
Bisschops et al.

(10) Patent No.: US 9,012,212 B2
(45) Date of Patent: Apr. 21, 2015

(54) METHOD AND DEVICE FOR CONTINUOUS MEMBRANE ADSORPTION

(75) Inventors: Marc Antonius Theodorus Bisschops, Breda (NL); Jozef Anton Mari Pennings, Den Haag (NL); Jacob Arthur Tijsterman, Haarlem (NL)

(73) Assignee: Xendo Holding B.V., Leiden (NL)

( * ) Notice: Subject to any disclaimer, the term of this patent is extended or adjusted under 35 U.S.C. 154(b) by 734 days.

(21) Appl. No.: 12/596,390

(22) PCT Filed: Apr. 17, 2007

(86) PCT No.: PCT/NL2007/000103
§ 371 (c)(1),
(2), (4) Date: Feb. 2, 2010

(87) PCT Pub. No.: WO2008/127087
PCT Pub. Date: Oct. 23, 2008

(65) Prior Publication Data
US 2010/0144028 A1    Jun. 10, 2010

(51) Int. Cl.
*C12N 15/86* (2006.01)
*C07K 1/18* (2006.01)
*B01D 15/18* (2006.01)
*C07K 1/22* (2006.01)
*C07K 1/36* (2006.01)
(Continued)

(52) U.S. Cl.
CPC .............. *C07K 1/18* (2013.01); *B01D 15/1807* (2013.01); *B01D 15/1821* (2013.01); *B01D 15/1864* (2013.01); *C07K 1/22* (2013.01); *C07K 1/36* (2013.01); *G01N 30/468* (2013.01); *G01N 2030/527* (2013.01)

(58) Field of Classification Search
None
See application file for complete search history.

(56) References Cited

U.S. PATENT DOCUMENTS 4,533,398 A      8/1985   Neuzil et al.
5,156,736 A  *  10/1992   Schoenrock ................... 210/264
(Continued)

FOREIGN PATENT DOCUMENTS

DE            19629208      *  7/1996   ............. B01D 15/08
DE          196 29 208 A1     1/1998
(Continued)

OTHER PUBLICATIONS

Roper et al (1995) J Chrom 702: 3-26.*
(Continued)

*Primary Examiner* — Chris L Chin
*Assistant Examiner* — Richard Moerschell
(74) *Attorney, Agent, or Firm* — Leydig, Voit & Mayer, Ltd.

(57) ABSTRACT

A method and system is provided for yielding biopharmaceutical products involving a chromatographic separation process. The method comprises: providing a plurality of membrane adsorber cartridges; providing a plurality of valves, communicatively coupled to said plurality of membrane adsorber cartridges; and switching the valves, so as to interconnect said membrane adsorber cartridges to operate in a countercurrent flow mode. The system comprises multiple membrane adsorber cartridges that are interconnected and configured to operate in a countercurrent flow mode. Furthermore, the configuration comprises a valve assembly that allows the cartridges to be subjected to different steps in the process by automatic switching of the valves. In this way, cartridges are recycled many times during the purification of a batch.

15 Claims, 15 Drawing Sheets

(51) Int. Cl.
*G01N 30/46* (2006.01)
*G01N 30/52* (2006.01)

(56) References Cited

U.S. PATENT DOCUMENTS

| | | | |
|---|---|---|---|
| 6,284,883 B1 * | 9/2001 | Mills, Jr. | 536/25.4 |
| 6,287,461 B1 | 9/2001 | Demmer et al. | |
| 2004/0241878 A1 * | 12/2004 | Thommes et al. | 436/514 |
| 2007/0131615 A1 * | 6/2007 | Moran et al. | 210/656 |
| 2009/0050567 A1 * | 2/2009 | Aumann et al. | 210/657 |

FOREIGN PATENT DOCUMENTS

| | | |
|---|---|---|
| EP | 1 310 790 A | 5/2003 |
| JP | 2000-193669 A | 7/2000 |
| JP | 2000-515802 A | 11/2000 |
| WO | WO 01/37959 * | 5/2001 ............ B01D 15/02 |
| WO | WO 01/37959 A | 5/2001 |
| WO | WO 2006/039528 A1 | 4/2006 |
| WO | WO 2006/116886 * | 9/2006 ............ B01D 15/18 |
| WO | WO 2006/116886 A | 11/2006 |
| WO | WO 2007/043874 A | 4/2007 |
| WO | WO 2007/110203 A | 10/2007 |

OTHER PUBLICATIONS

Ludemann-Hombourger (2002) J Chrom A, 947: 59-68.*
Roper et al., "Seperation of biomolecules using adsorptive membranes," Journal Of Chromatography A, vol. 702, No. 1. pp. 3-26, (May 19, 1995).
International Search Report for PCT/NL2007/000103, dated Jan. 17, 2008.

* cited by examiner

US 9,012,212 B2

METHOD AND DEVICE FOR CONTINUOUS MEMBRANE ADSORPTION

FIELD OF THE INVENTION

The invention relates to a method and device for chromatographic separations. In particular, the invention relates to a membrane adsorption system that is suitable for purification of biopharmaceutical products.

BACKGROUND OF THE INVENTION

The production of biopharmaceutical products normally involves a cultivation process of bacteria, yeasts, animal, plant, and/or transgenic cells. The fermentation or cultivation process produces a broth that contains the biomass, the desired product and many other components in solution. Among the other components, one may find contaminants and product related impurities. These may, for example, include media components (antibiotics, glucose, amino acids), viruses, endotoxins, DNA, aggregates and host cell proteins.

In order to produce the biopharmaceutical product with the required safety and efficacy requirements, typically, multiple purification steps are used to remove the contaminants and product related impurities. Two modes of operation can be distinguished for chromatographic processes:

Flow Through; the process solution is passed through the chromatography bed and one or more contaminants bind to the resin. The process solution, with the product of interest dissolved in it, passes through the bed and is collected with a significant reduction in contaminants;

Bind & Elute: the product of interest is preferentially bound to the resin and the process solution with the majority of contaminants dissolved will pass through the bed. The product of interest is then eluted in a later stage and can be collected highly purified.

The advantages of membrane adsorbers have been successfully exploited in Flow Through operations. For Bind & Elute type of chromatography, however, the nature of membrane adsorbers represents a few significant disadvantages, in particular, its low volumetric capacity: the amount of product that can be bound to a membrane adsorber per unit volume of membrane material. Accordingly, a desire exists to provide a method wherein the membrane absorbers can be used while improving the yield of a product of interest.

SUMMARY OF THE INVENTION

According to one aspect of the invention, a method is provided for yielding biopharmaceutical products involving a chromatographic separation process, the method comprising: providing a plurality of membrane adsorber cartridges; providing a plurality of valves, communicatively coupled tot said plurality of membrane adsorber cartridges; and switching the valves, so as to interconnect said membrane adsorber cartridges to operate in a countercurrent flow mode.

According to another aspect of the invention, a chromatographic system is provided comprising: a plurality of membrane adsorber cartridges; a valve assembly communicatively coupled to the plurality of membrane adsorber cartridges; and a processor arranged to control switching of the valves, wherein the membrane adsorber cartridges are interconnected and configured to operate in a countercurrent flow mode.

By using membrane absorbers in combination with the system described herein, the process economy of using these membrane adsorbers becomes more competitive to packed beds, even when the membrane adsorbers are designed for single-use (as a disposable).

BRIEF DESCRIPTION OF THE DRAWINGS

FIGS. 7, 8 and 9 depict various detailed section views of a duct layout part depicted in

FIG. 6;

DESCRIPTION

Figure 1:
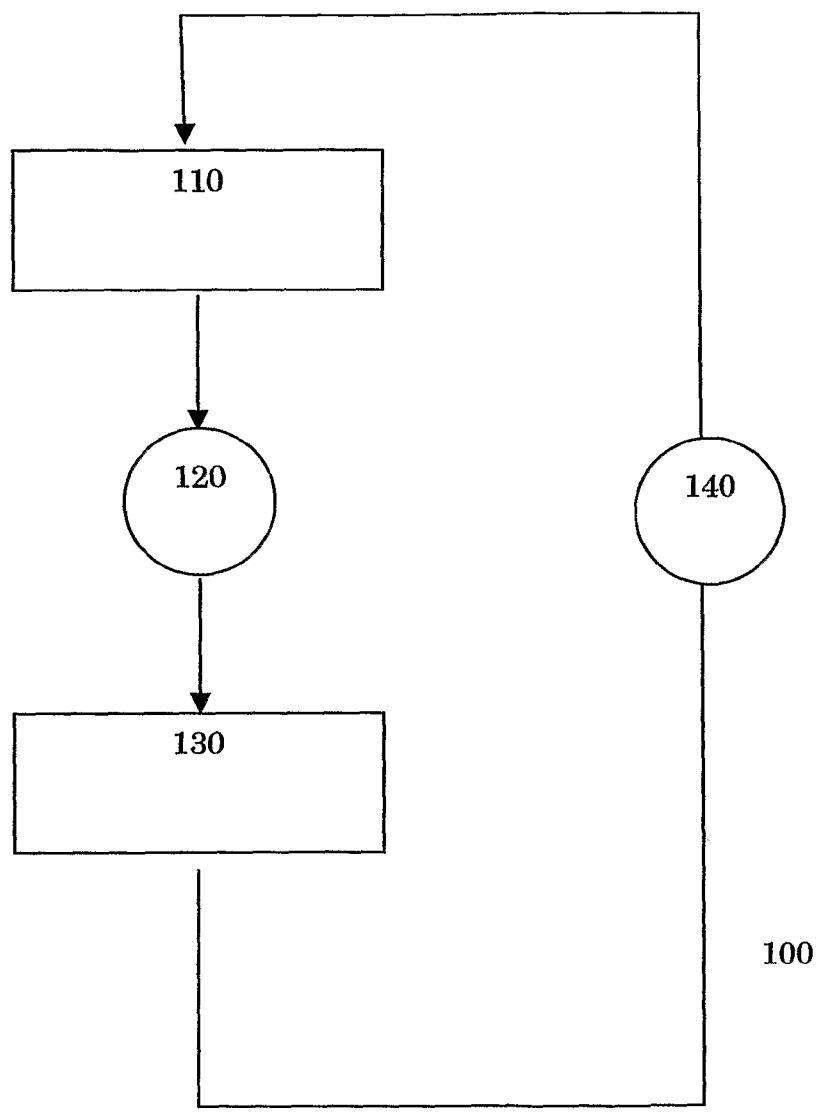
FIG. 1 schematically depicts an iterative process for obtaining a biopharmaceutical product.

Both for Bind & Elute and for Flow Through operations, packed bed chromatography is common practice. Packed bed chromatography, however, suffers from a few major disadvantages. The most eminent disadvantage is represented by the fact that packed bed chromatography cannot tolerate very high linear flow rates. In many cases, the throughput of continuous chromatography processes is limited by the hydraulic capacity of the packed beds rather than by process kinetics or binding capacity constraints.

As a consequence, the column diameter is determined by the volumetric throughput of the process. For large-scale monoclonal antibody production processes, columns up to 2 meter in diameter have been reported. The volume of resin that is required to pack columns with such large diameters can go up to several hundreds of liters, which is much more than needed to capture all trace amounts from the solution in Flow Through mode.

For this reason, membrane adsorbers are being applied for Flow Through chromatography more and more. The fundamental properties of membrane adsorbers are—among others—described by Roper and Lightfoot (Journal of Chromatography A (1995) 702, pp. 3-26), C. Boi et al. (J. Of Chrom. A. (2007), doi: 10.1016/j.chroma.2007.02.008) and Charcosset (Biotechnology Advances, 24 (2006) pp. 482-492). Membrane adsorbers are essentially identical to normal flow filtration membrane systems, in which the membrane material is functionalized with a ligand. This gives the membrane adsorber the ability to bind components from the solution that is passed through the membrane. As a consequence, membrane adsorbers basically combine the functionality of chromatography beds with the hydrodynamic characteristics of normal flow filtration membranes.

Nowadays, the majority of membrane adsorbers are designed for single-use (as a disposable format). This means that the entire cartridge is designed to be used for processing one single batch only. Once the batch of process solution has been processed, the cartridge is taken out of operation and disposed of. For Flow Through operations, this has the advantage that the membrane adsorber does not need to be washed and regenerated for reuse. This approach has resulted in a few additional advantages of using membrane adsorbers instead of packed bed chromatography for Flow Through operations. The most important advantages are the reduction in capital expenses, and the elimination of validation work and costs (e.g. Gottschalk et al., Bioprocess International, May 2004, pp. 56-65).

An example of a Flow Through process is the following. In order to remove trace amounts of contaminants, Flow Through chromatography is often used. Examples of contaminants in monoclonal antibody production are DNA, viruses and endotoxins. Many of these contaminants are negatively charged under neutral pH conditions, whereas the monoclonal antibody product is essentially neutral in charge. This allows the contaminants to be bound to an anion exchange resin, such as Q Sepharose FF (from GE Healthcare) or equivalent products. In such process, the solution containing the monoclonal antibody and the trace contaminants is passed through the column that is packed with the anion exchange resin. The monoclonal antibody product does not bind to the resin and passes through the column with the process solution. The resin inside the column binds certain categories of trace contaminants thereby removing them from the process solution that contains the monoclonal antibody product.

In Flow Through chromatography, typically, membrane adsorbers are applied in the "polishing" of the product solution, where the amount of trace contaminants and product related impurities in the process solution is reduced to very low levels. In such case, the volumetric binding capacity of membrane adsorbers is sufficient to capture such trace contaminants and product related impurities. The relatively high dead volume also is of relatively little importance, since in such polishing operation, the membrane adsorbers do not need to be washed and eluted before the product is collected.

An example of a Bind & Elute process in the purification of monoclonal antibodies is represented by the capture process in Protein A chromatography. The clarified supernatant of the cultivation process contains the dissolved monoclonal antibody, which generally represents 1-30% of the dissolved material. The solution is passed through the Protein A chromatography bed and the monoclonal antibodies bind to the Protein A ligand on the chromatographic media. The process solution flows through the bed and leaves the column essentially free from monoclonal antibodies. Once the column is saturated with monoclonal antibodies, the column is washed to remove any non-specifically bound materials and eluted under different process conditions (generally at a lower pH). Under these eluting conditions, the monoclonal antibody is released from the Protein A media and can be collected at the outlet of the column. Normally, such Bind & Elute process results in a highly pure product that only contains trace amounts of contaminants and product related impurities.

With the increase in expression levels of monoclonal antibodies that have been achieved in the cultivation process over the past decade (e.g. Wurm, Nature Biotechnology, (2004) vol. 22, nr. 11, pp 1393-1398), the application of membrane adsorbers for Bind & Elute chromatography is in most cases economically and technically not feasible. Membrane absorbers suffer from following disadvantages:

Membrane adsorbers contain a relatively low volume of membrane material. Even very large membrane cartridges, that can handle very high flow rates, do not nearly contain as much membrane material as a packed bed contains chromatography media.

Relatively high dead volumes in the cartridges: even though the current membrane adsorbers are carefully designed for minimum holdup volume, the dead volume inside the cartridge is inevitably relatively large in comparison to the volume of membrane material. Bind & Elute operations require that the membrane adsorber is washed and eluted before the product can be collected. The dead volume then results in a reduction of efficiency and hence to a significant increase in the consumption of buffers and a reduction in product concentration.

According to one aspect of the invention, a method and configuration is provided comprising multiple membrane adsorber cartridges that are interconnected and configured to operate in a countercurrent flow mode. Furthermore, the configuration comprises a valve assembly that allows the cartridges to be subjected to different steps in the process by automatic switching of the valves. In this way, cartridges are recycled many times during the purification of a batch. Such configuration reduces the disadvantage of relatively large dead volumes, while providing an advantage of high linear flow velocities and lower backpressures. In addition, compared to packed bed chromatographic processes, a tedious preparation procedure of packing such packed bed columns can be circumvented, which is of great importance since continuous chromatography systems typically require multiple beds that are—within a certain range—reproducibly packed.

Turning to FIG. 1 schematically an iterative process 100 is shown of obtaining a biopharmaceutical product of interest. In a first binding action 110 a process fluid is provided in at least one membrane adsorber cartridge. The process fluid typically contains a component of interest, in particular, a biopharmaceutical product or precursor thereof and the membrane adsorber in the adsorber cartridge 31 (illustrated for example in FIG. 12-FIG. 16) has functionality for binding the component of interest to the membrane adsorber.

As an example, e.g, for the purification of recombinant protein products the membrane has adsorber functionality using affinity chromatography, ion exchange chromatography and/or mixed mode chromatography to bind and elute the product of interest, per se known in the art.

In another example, e.g. for the purification of DNA or viral vectors, said membrane adsorber cartridge has adsorber functionality using affinity chromatography, ion exchange or mixed mode ligands.

In yet another example, e.g. for the purification of monoclonal antibodies the membrane adsorber cartridge has adsorber functionality using protein A chromatography, cation exchange and/or mixed mode ligands.

After the binding action 110, the adsorber cartridge is switched to another fluid flow by a first switching action 120. This first switching action 120 includes switching at least one valve of the valve assembly to initiate an elution action 130.

The elution action 130 can comprise a number of pre- and post processing steps; it at least comprises a step of providing an elution fluid flow to elute the product of interest from at least one membrane adsorber. Thus, during elution 130, the product of interest is eluted from the at least one membrane adsorber and further yielded in a customary manner.

Figure 12:
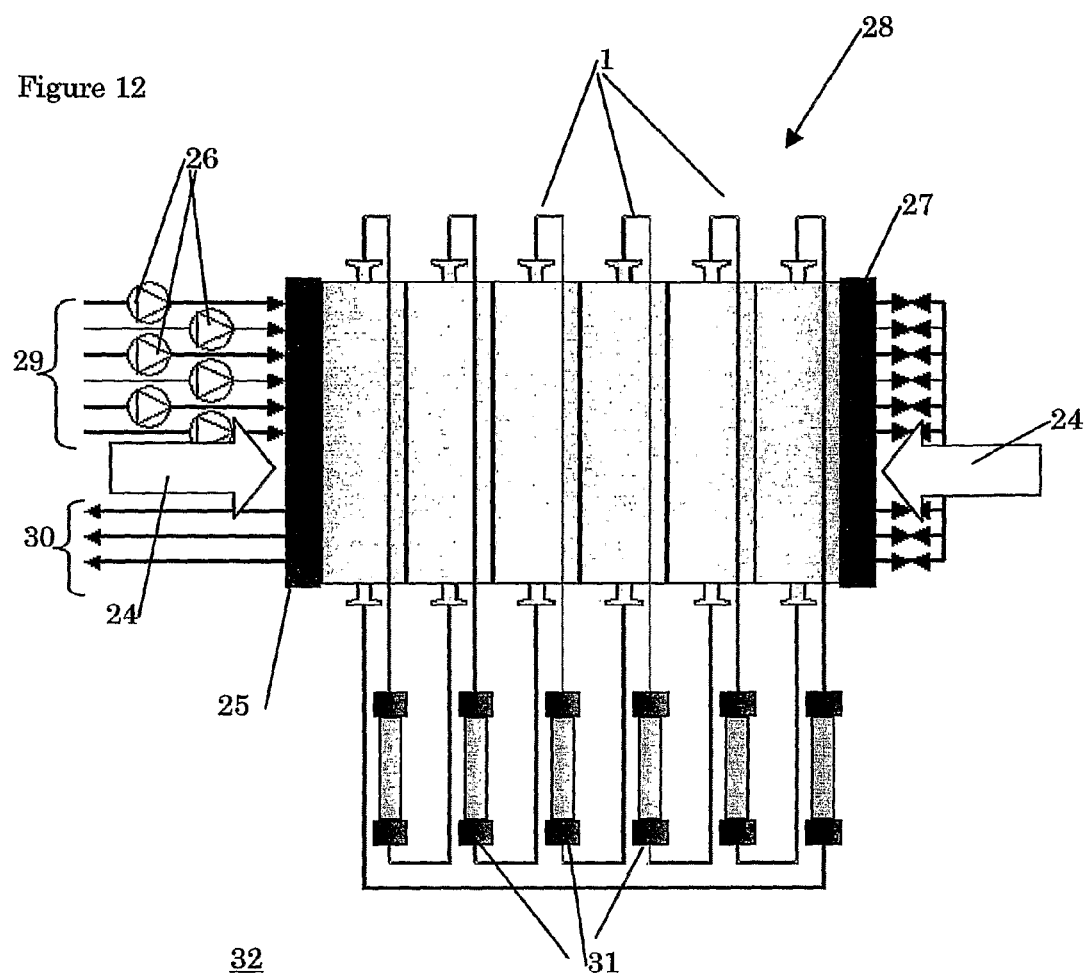
FIG. 12 depicts an exemplary embodiment comprising multiple manifolds pressed together to form a single valve unit.
Figure 13:
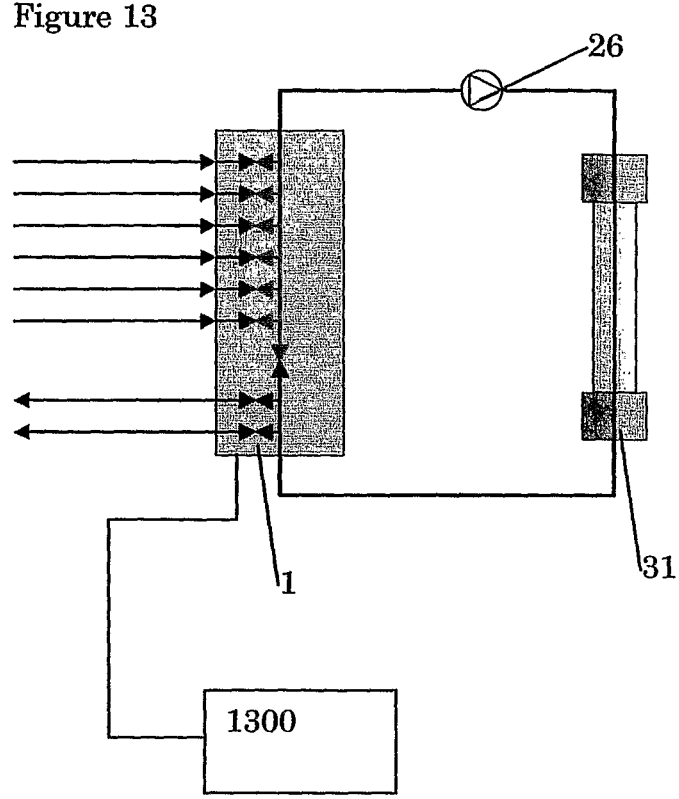
FIG. 13 schematically depicts a single cartridge set-up for performing chromatographic separations.

To control the switching actions 120, 140 of the valves, a processor 1300 is arranged (see FIG. 13). This processor 1300 essentially controls the fluid flows and directions thereof, by timely actuating a plurality of valves, preferably in the form illustrated further in FIG. 5-FIG. 16. In particular, the processor 1300 arranges the process fluid flow in binding action 110 and the elution fluid flow in action 130 to be in countercurrent flow mode.

A continuous countercurrent process is disclosed in WO 2004/024284. Each of the different fluids involved is connected to one inlet of the system. A valve is controlled in such a way that the cartridges are subsequently subjected to the binding, washing, elution, regeneration and equilibration to form a number of steps involved in a process cycle. Since multiple cartridges can be connected in series one or more of these steps can be carried out in essentially countercurrent mode. Through switching a simulated transport of the cartridges is provided in a direction opposite a direction of flow of the processing fluid. This enables a more efficient process and may lead to significant savings in chemicals, solvents and water. After elution action 130 a second switching action 140 is performed including switching at least one valve of the valve assembly to repeat said binding action 110 in an iterative way, until a predetermined stopping criterion is reached, which may be a time period or a concentration criterion of a specific product or fluid used during the biopharmaceutical product yielding process 100.

Figure 2:
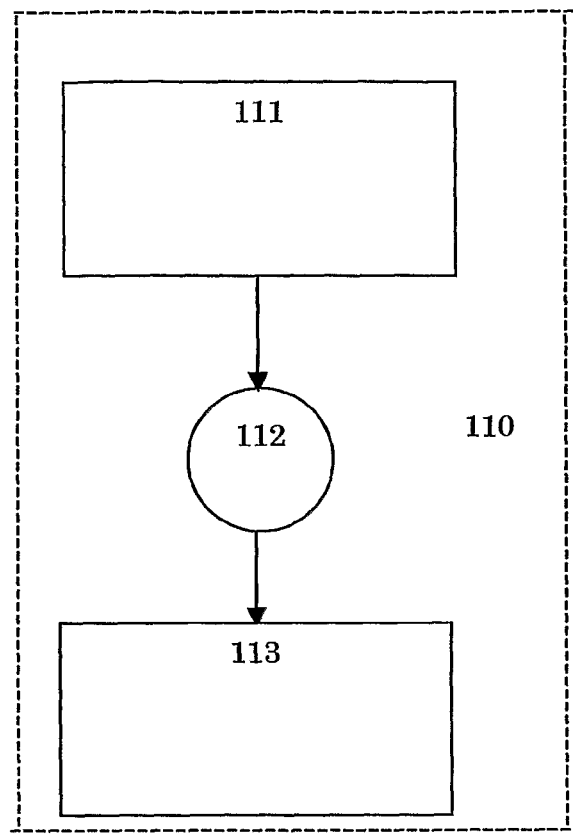
FIG. 2 schematically depicts pre and post processing steps for a binding action.

In a preferred mode, FIG. 2 shows that the binding action 110 can also comprise a number of pre- and post processing steps, i.e. it may include a number of associated actions, in particular a regenerating action 111 as a preprocessing action, that is, an action executed prior to providing the process fluid to the membrane adsorber cartridge for binding a component of interest including providing at least one regenerating fluid in said at least one adsorber cartridge to the membrane adsorbers. After the regeneration action 111, a third switching action 112 is performed including switching at least one valve of the valve assembly to initiate providing of said process fluid for binding the component of interest in step 113.

Typically, the regenerating fluid has functionality to clean, sanitize and/or strip and/or equilibrate the membrane adsorbers prior to binding the component of interest, so that the membrane adsorbers do not wear out in the iterative process, but can be used repeatedly as long as possible.

Figure 3:
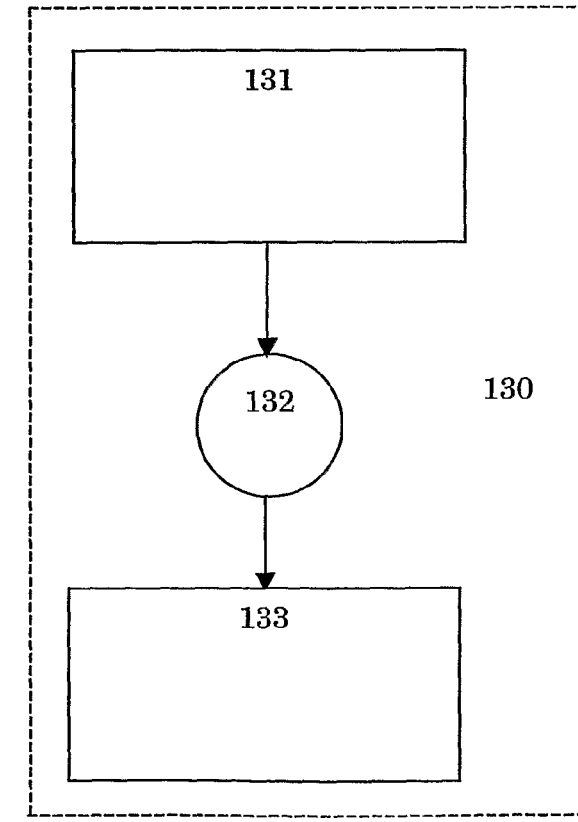
FIG. 3 schematically depicts pre and post processing steps for an elution action.

Also, with reference to FIG. 3, the elution action 130 may further comprise a number of pre- and postprocessing step, in particular, preferably includes a washing action 131. The washing action 131 typically includes providing a buffer in said membrane adsorber cartridge to displace the process fluid from dead volume present in said at least one membrane and replace the process fluid in the adsorber cartridge by said buffer fluid. After washing action 131, a fourth switching action 132 is performed including switching at least one valve of the valve assembly to initiate providing said elution fluid flow in step 133.

Figure 4:
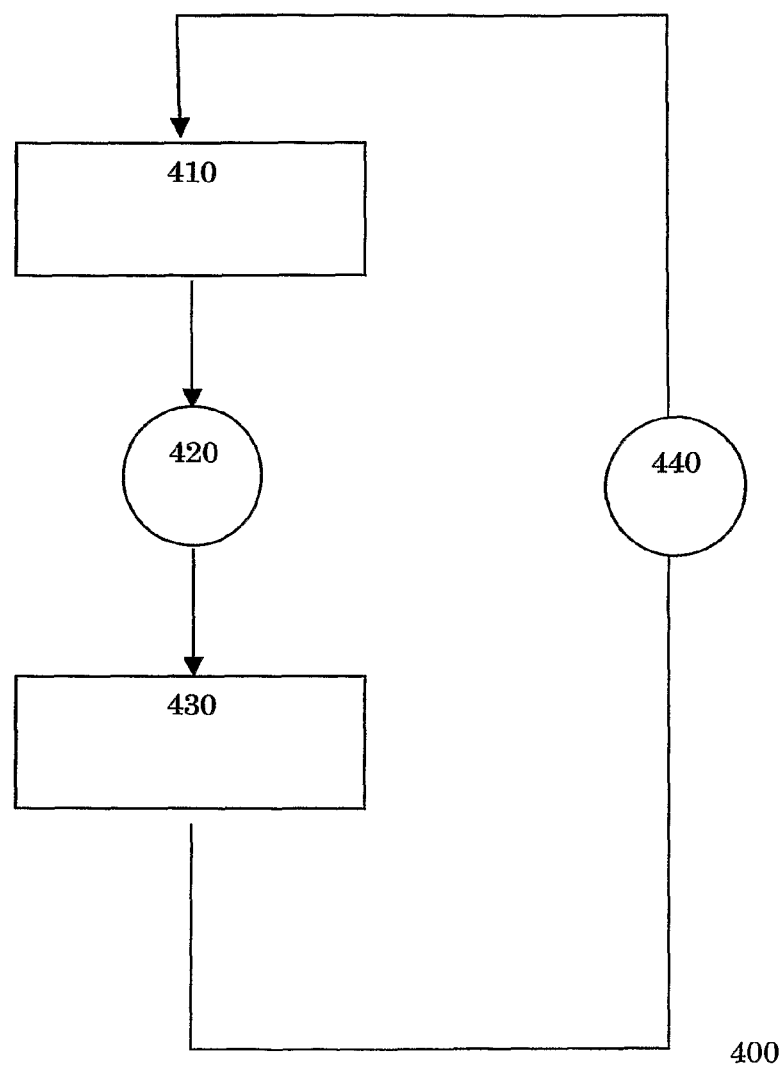
FIG. 4 schematically depicts an alternative iterative process for obtaining a biopharmaceutical product.
Figure 5:
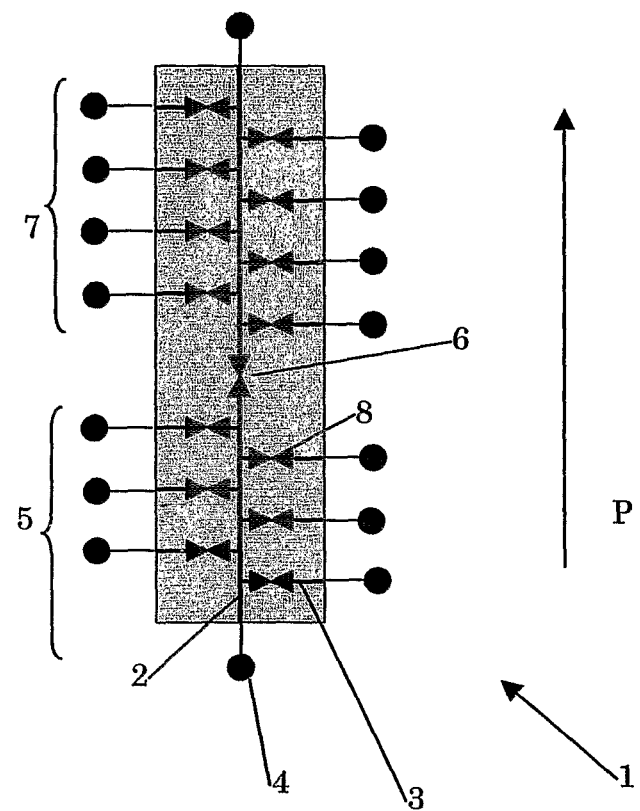
FIG. 5 depicts a manifold suitable for use in a system for carrying out the iterative process.

FIG. 4 shows an alternative embodiment of the example process flow depicted in FIG. 1. In this process flow 400, iteratively, a purification process is performed to obtain a purified biopharmaceutical product of interest. The process steps are similar to the FIG. 1 embodiment, however, in the first binding action 410, instead of binding the product of interest as in the process depicted in FIG. 1, a process fluid is provided to a membrane adsorber cartridge that has functionality for binding a group of contaminants to the membrane adsorber provided in said membrane adsorber cartridge. After the binding action, typically, after a predetermined time or when a critical process parameter reaches a certain value, a switching action 420 is performed including switching at least one valve of the valve assembly to initiate a regenerating action 430. The regenerating action includes providing at least one regenerating fluid in said at least one adsorber cartridge to the membrane adsorbers prior to the binding action. In this way, the membrane adsorbers are regenerated optimally; so that the membranes can be used for a long time without wear. Typically, the regenerating fluid has desorbing functionality to desorb the contaminant from the at least one membrane adsorber in a countercurrent contact mode. In this way, the contamination is extracted from the membranes in a most efficient and time-effective way. Further, preferably, the regenerating fluid may have functionality to clean and/or strip and/or equilibrate the membrane adsorbers prior to binding the component of interest.

In addition, the binding action 410 and regenerating action 430 may each include a number of pre- and postprocessing steps 440, for instance, by providing functionality through a plurality of fluids that may be provided to the adsorber cartridge in a number of subsequent valve switching actions (not shown).

As an example, this process 400 can be used for the polishing of monoclonal antibodies, recombinant proteins, viral vectors or DNA products.

In another aspect of the invention such a valve cassette is a device for chromatographic separations comprising a manifold comprising a plurality of connectors for connecting to one or more chromatographic separation cartridges and/or feed or extraction tubing wherein at least one central duct is provided between at least two connectors forming an inlet and an outlet respectively. The central duct comprises a closable duct valve. In addition, a plurality of branch ducts branching from the central duct to a branch connector are provided, the branch duct comprising a closable branch valve. At least one branch duct is positioned between the inlet and the central duct valve and at least one branch duct is positioned between the outlet and the central duct valve.

According to another aspect of the invention, the system comprises one or more adsorber cartridges, at least one of which is connected to a valve manifold at the in- and outlets. Furthermore, the system may comprise multiple inlets and outlets. System inlets may be connected to a pump capable of transferring any of the fluids involved into the chromatography process. Alternatively, a system outlet can be connected to the inlet of a subsequent step in the purification process, such as a membrane unit or another chromatography step. For convenience, additional monitors may be connected to the system in- and outlets to monitor relevant process conditions, including (but not limited to) pressure, conductivity, pH or UV absorbance or other critical process parameters.

Figure 6:
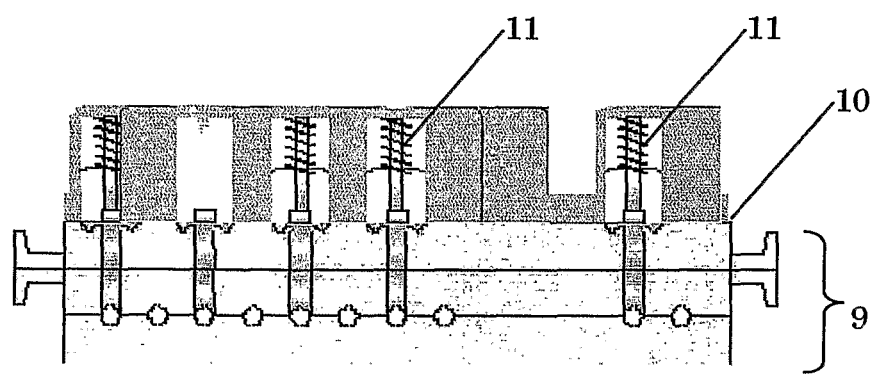
FIG. 6 depicts duct layout and diaphragm parts of an exemplary manifold for carrying out the iterative process.

Although the valve device can be construed in a variety of ways, in one aspect, the valve device according to the invention preferably comprise two or three separate construction parts as shown in FIG. 6 and further detailed in FIG. 7-FIG. 10. This valve arrangement has the advantage of simple and cost-effective construction, allowing for single use purpose. In addition, the dead volume in the valve arrangement is very small, typically, depending on the configuration, several milliliters, or at most 2% of the cartridge volume, providing effectively a zero dead volume. In this arrangement, preferably, zero-dead-leg valves are used.

In such embodiment (see FIG. 5), a manifold 1 comprises a central duct 2 connectable to an outlet of a cartridge (see for instance the arrangement depicted in FIG. 12) and an inlet of a cartridge. Branch ducts 3 are connectable to system in- and outlets such as feed flows and extraction flows. In addition, depending on the system configuration, the branch ducts 3 may be coupled to cartridge in- and outlets. In general, the central duct 2 provides an efficient flow connection between subsequent cartridges to be coupled serially and/or parallel by connectors 4, to minimize flow impedances, in particular of the main flow between cartridges, in the manifold 1. Preferably, system inlets and outlets (not shown) are connected to a branch duct 3 that connects to the central duct 2. In the embodiment shown, the manifold 1 can be coupled to membrane adsorber cartridges. In such an arrangement, the branch connectors 5 are forming system extraction outlets, separated by a central valve 6 in the central duct 2 from branch connectors 7 forming feed inlets. In addition, the branch ducts 3 are separated from the central duct 2 by branch duct valves 8. Typically, the connectors can be of any type, and are preferably of a sanitary type such as a connector known in the art as a tri-clover connector. Although the schematic drawing depicts the connectors as protruding elements, alternatively, the connectors can be of a male-female type. Yet as another alternative, the connectors can be of a gasket type.

A preferential type of valve, for both central valve and branch duct valves, is a diaphragm valve which is shown as an exemplary embodiment in FIG. 10. This type of valve has a simple geometry and optimally designed wet surfaces which makes it preferable of use in chromatographic processes for biopharmaceutical products, which has a very high requirement on sanitary parts. In this respect, the term "optimally designed" refers to a condition that there is a minimum of dead space and complex geometry which is cumbersome in view of sanitary requirements. However, the invention is not limited to such valves but could incorporate other valves with like sanitary characteristics:

As an example, a typical layout for the valve manifold 1 and parts thereof is shown in FIG. 6 to FIG. 10. It may be clear that many alternative configurations and designs can be thought of, which fulfill the same requirements. The drawings included in this document only serve as an illustration. The invention is not limited to the design shown here.

In one aspect of the invention, as shown in FIG. 6, the manifold 1 is formed from a duct layout part 9 and a diaphragm 10 for closing the duct layout part 9 and for forming the diaphragm valves, and comprising mountings for mounting a corresponding number of actuators 11.

Figure 7:
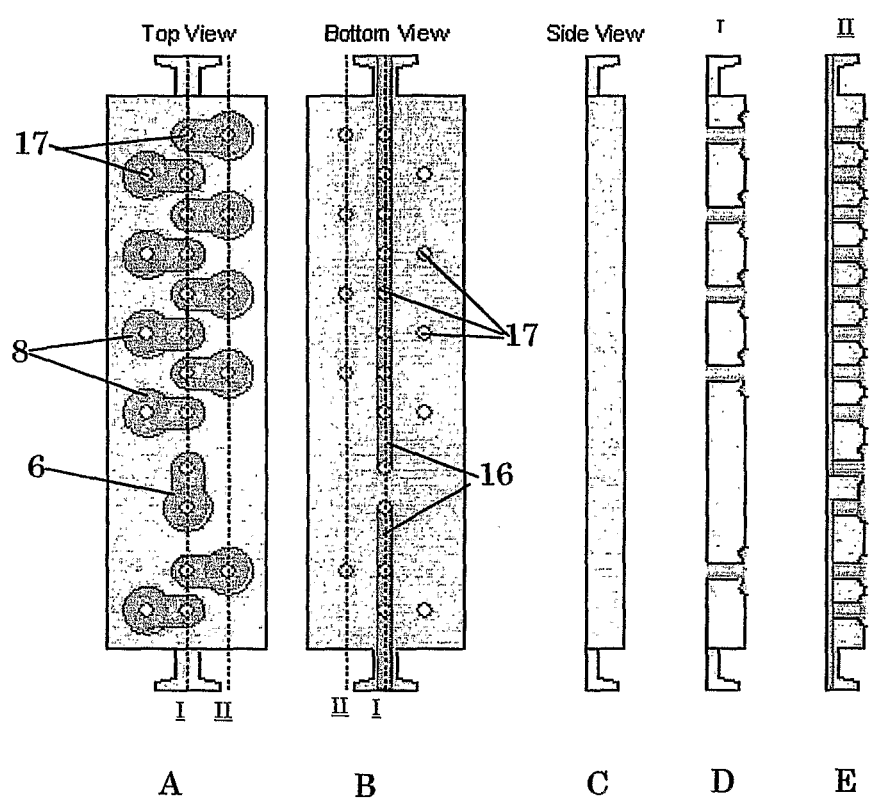
Figure 8:
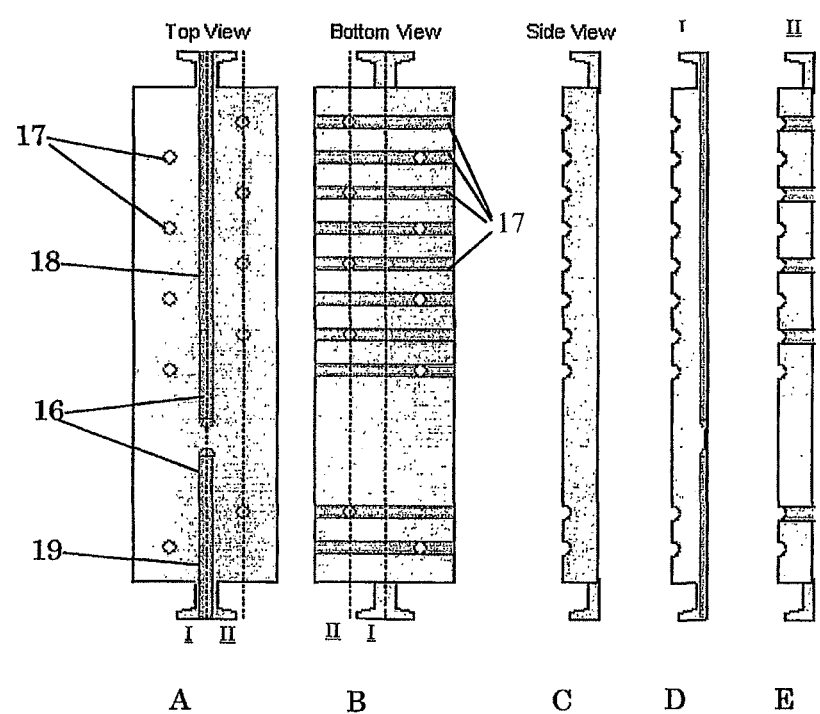
Figure 9:
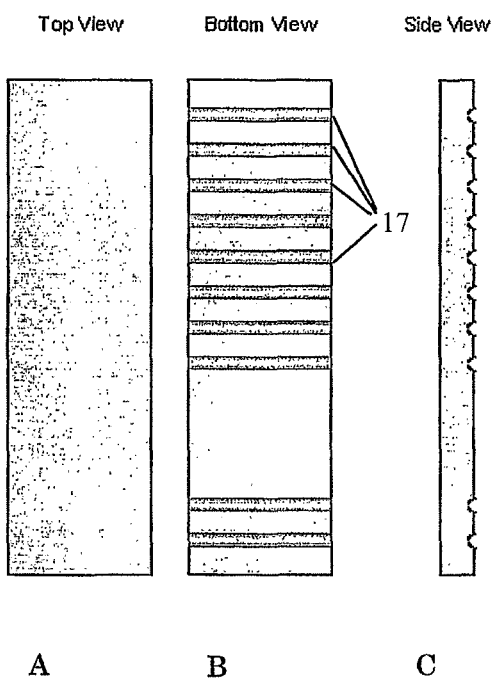

As shown in the subsequent FIG. 7-FIG. 9 the duct layout part 9 comprises a central part 12 (illustrated in FIG. 8) coupled between a base part 13 (FIG. 9) and a cover part 14 (FIG. 7); one side of the central part 12 corresponding a branch duct structure 15; and an opposite side of the central part 12 corresponding to a central duct structure 16, the central part 12 comprising through holes 17 to correspond with through holes 17 provided in a cover part 14; the cover part 14 being coupled to the diaphragm 10 for closing a through hole 17 so as to form a diaphragm valve 8 between the central duct structure 16 and the branch duct structure 15. In the figures, for reasons of clarity, only a limited number of items is identified and corresponding items are not individually referenced.

Specifically, FIG. 7 and FIG. 8 show, from left to right, a top view (A), a bottom view (B), a side view (C) and cross sectional views D and E through sections I-I and II-II respectively indicated in the top and bottom views A and B. FIG. 9 shows, from left to right a top view (A), a bottom view (B) and side view (C).

It can be seen in FIG. 7 and FIG. 8 that the central duct structure 16 is formed by ducts 18 and 19 that are connected, via the trough holes 17, and the central duct valve 6.

In addition, the cover part 14 may also contain the diaphragm 10 of these valves. Alternative, the diaphragm 10 can be provided by a separate construction part. The diaphragm 10 comprises a flexible diaphragm 20 (see FIG. 10) that can close or open the connections between the system in- or outlets and the cartridge in- or outlets in this part of the manifold 1.

In the said example, the cover part 14 may be arranged to carry actuators 11 that can press or release the membranes against said duct layout part 9, thereby opening or closing a diaphragm valve 8. These actuators 11 can be of any kind. Commonly used actuators operate on electromagnetic force or pneumatic pressure.

Figures 10A, 10B:
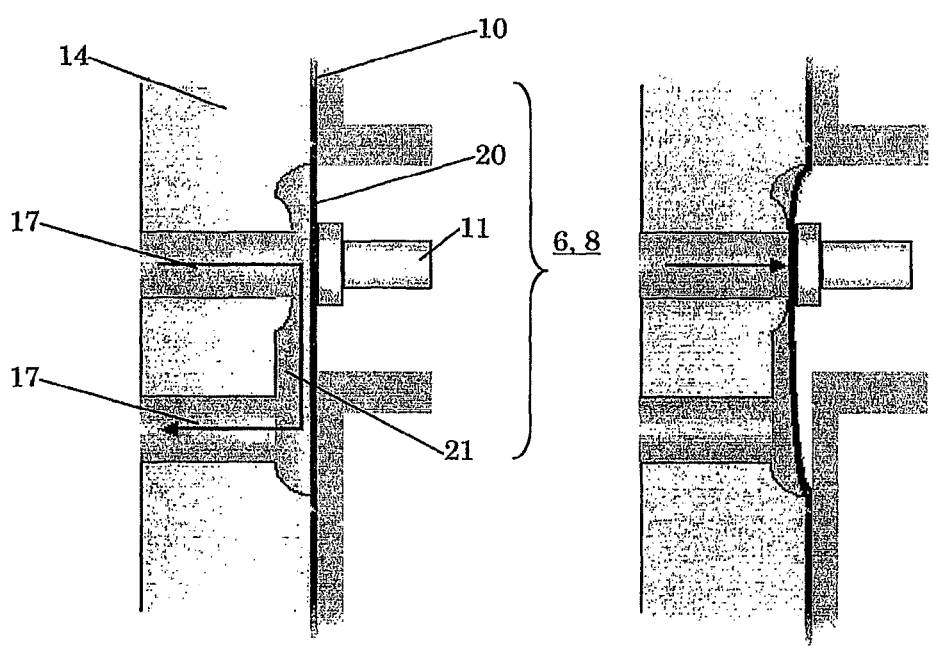
FIG. 10 depicts a close-up view of the diaphragm-duct layout interface of the manifold.

FIG. 10 shows in more detail the construction of a valve diaphragm 6 and/or 8 according to the invention. In FIG. 10A, the valve is shown in an open position, in FIG. 10B, the valve is shown in a closed position. Here, the cover part 14 is shown to have through holes which are in fluid communication with the branch ducts (not shown) and central duct (not shown). The through holes 17 are formed in a pocket 21 which is covered by a flexible diaphragm 20. By pressing the diaphragm 20 in the pocket 21, the flow through the through hole is stopped and the valve 8 is closed.

In case said first part does not already include a diaphragm that can close or open the connections between the system in- or outlets and the cartridge in- or outlets in this part of the manifold 1, the manifold 1 may comprise a third part which comprises or which carries the diaphragm 20.

Once assembled together, the two or three parts (base part 13, central part 12, cover part 14) combine to one manifold 1 with multiple diaphragm valves 8. The diaphragm valves 8 each may have their own actuator 11 and may each be individually controlled.

The only wetted parts in the valve manifolds are the duct layout part 9 and—if applicable—the diaphragm 10, being the diaphragm 20 of the diaphragm valves 8. These parts of the valve manifold are preferably designed for single-use or dedicated-use.

Figure 11:
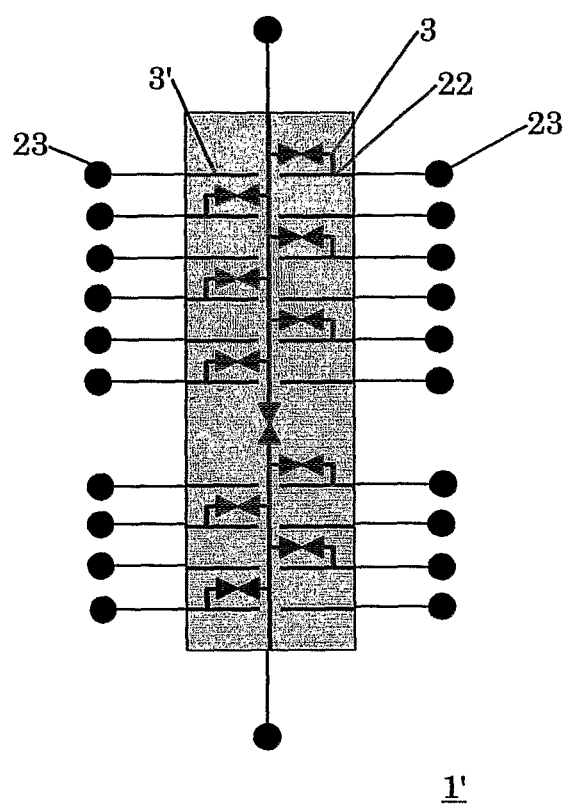
FIG. 11 schematically depicts the arrangement of inlets/outlets of the manifold.

In one aspect of the invention, the system inlets and system outlets of each manifold 1' actually pass through the manifold as is schematically depicted in FIG. 11. That is, preferably, at least one branch duct 3 comprises another branch 22 to form a branch duct 3' between at least two branch connectors 23, the branch duct 3' in fluid communication and closable from the central duct 2. This allows connecting manifolds to each other without a separate distributor. Each of the system in- and outlets is connected to one end of a series of manifolds, while the other end of the series can be closed by a valve or may be permanently closed. This connection between two subsequent manifolds can be done by sanitary couplings between the different in- and outlets, for instance through tri-clover connections. In that case, every system in- and outlet requires one clamp between two adjacent manifolds.

Alternatively, a pocket for the gasket can be molded in the side surfaces of the manifold in such a way that these gaskets ensure leak-tight connections between the adjacent manifolds. In this case, the manifolds should be tightly pressed together by some means such as a press 24 or the like as is schematically depicted in FIG. 12. Yet another alternative is that the gaskets of all connections are combined in one layer that should be put in between two adjacent manifolds. In such a case, the manifolds may be equipped with a fitting to ensure proper positioning of the gasket. In this case, the sealing is again ensured by pressing the manifolds tightly together. This can, for instance be done, by enclosing the manifolds between a front member 25 that connects all system in- and outlets towards pumps 26, vessels, containers, etc. and a rear member 27 that may contain (manual) valves or that may even close all in- and outlets from the last manifold. Said front and rear members 25, 27 are firmly pressed together, thereby pressing all manifolds together and ensuring proper sealing of the connections between these manifolds. FIG. 12 shows an exemplary embodiment of a multiple of manifolds 1 pressed together to form a single valve unit 28 comprising of modular pieces 1. The valve unit 28 is coupled between system inlets 29 and outlets 30 and cartridges 31 coupled to form a chromatographic separation system 32.

In one aspect of the invention, the system consists of three cartridges with valve manifolds in between them. Each of these manifolds has minimal three inlets and minimal two outlets. This combination allows continuous a process as normally conducted in a merry-go-round system. This involves continuous feeding of at least one cartridge, generally two cartridges in series. The third cartridge is washed, eluted and/or regenerated while the first and second cartridge are being loaded. After a certain time, once the first cartridge is saturated, the valves in the manifolds switch in such a manner that the feed solution is applied on the second cartridge, while said first cartridge is subjected to all other steps in the process. The third cartridge is connected to the outlet of the second cartridge.

In one aspect of the invention, the system comprises four to eight cartridges with valve manifolds in between them. Each of these manifolds comprises at least three inlets and at least three outlets. This combination allows continuous fractionation processes. Since the valves are controlled individually, the length of the different zones does not necessarily have to be constant during the operation and not all flow rates are necessarily constant over the entire process cycle.

In one aspect of the invention, the system comprises eight or more cartridges with valve manifolds in between them. Each manifold has minimal five, preferably eight inlets and minimal two, preferably four outlets. This combination allows continuous countercurrent purification of complex proteins, such as monoclonal antibodies, using ion exchange or affinity chromatography.

In one aspect of the invention, the system comprises a single cartridge and a single valve manifold. A pump is connected to the cartridge inlet of the valve manifold and transfers the fluids from the valve manifold to the cartridge inlet. The cartridge outlet is connected to the cartridge outlet of the valve manifold. The system inlets and system outlets are connected to respectively product or waste collection tanks. This system allows conducting traditional single cartridge chromatographic purifications with one disposable valve manifold. The valves are controlled such that all process solutions are pumped into the cartridge in the appropriate order. The valve that connects the cartridge inlet and cartridge outlet in the valve manifold remains closed at all time.

In one aspect of the invention, the system comprises multiple cartridges, each carrying a different Adsorbent. This allows conducting fully automated multi-step chromatographic purifications. This may or may not involve intermediate storage connected to the system outlets, which is also connected to a system inlet.

EXAMPLES

With reference to FIG. 13 a single cartridge set-up is shown for performing chromatographic separations using a membrane adsorber cartridge 31. The assembly consists of one membrane adsorber cartridge 31, one manifold 1 and one pump 26. The pump 26 is used to transfer fluids from the valve manifold 1 towards the cartridge 31. The valve manifold is used to select the appropriate solution from the storage containers (not drawn) and to direct the cartridge effluent to either waste or product collection container (not drawn). During normal operation, the central valve 6 of the valve manifold 1 is closed. This scheme can involve as many inlets and outlets as required for the separation.

The processor 1300 is arranged to control switching of the valves in manifold 1. The manifold is preferably of the type illustrated with reference to FIG. 6-FIG. 10 since this has wetted parts that are disposable. In particular, the manifold is actuated by actuators (not shown), that are controlled by the processor 1300. The actuators can push the diaphragm 20 of the diaphragm valves in open or closed positions, effectively controlling the valve switching action.

Figure 14:
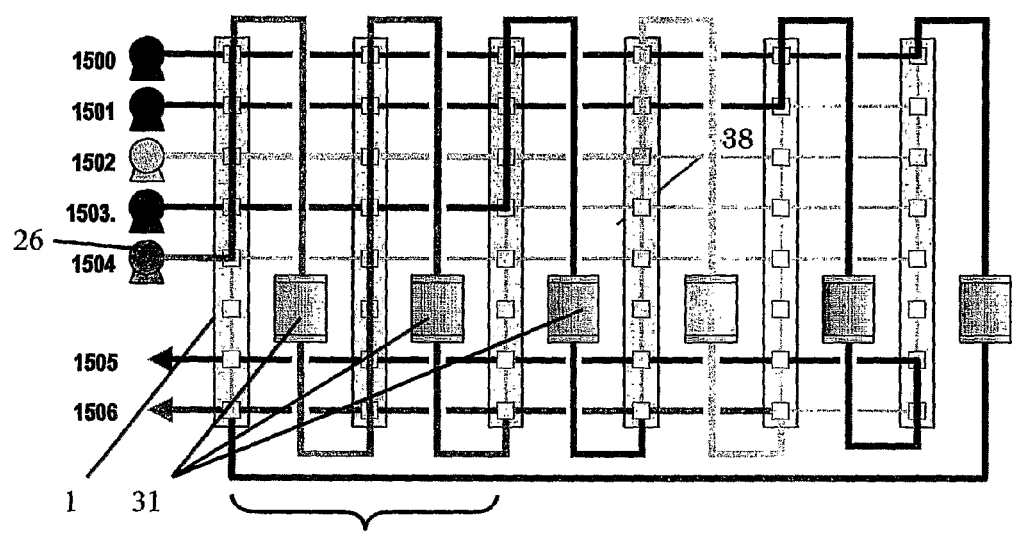
FIGS. 14 and 15 schematically depict various states of a system for carrying out bind and elute chromatographic separation in a manifold system including five pumps and six valve manifolds.
Figure 15A:
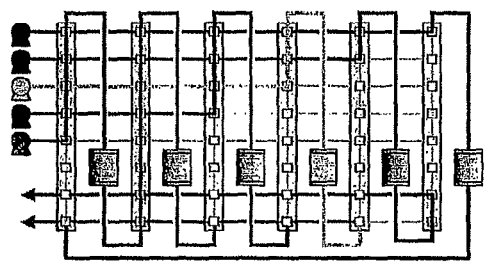
Figure 15B:
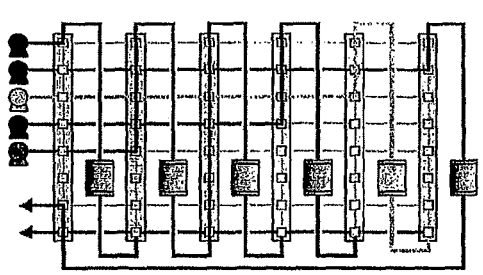
Figure 15C:
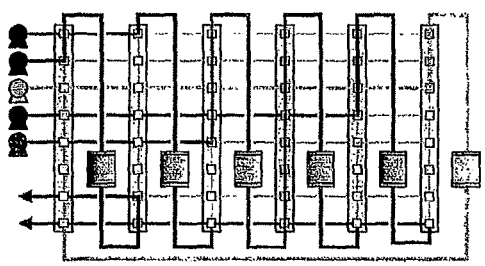
Figure 15D:
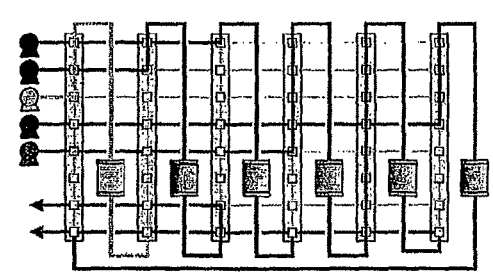
Figure 15E:
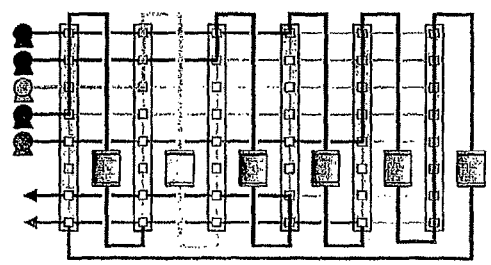
Figure 15F:
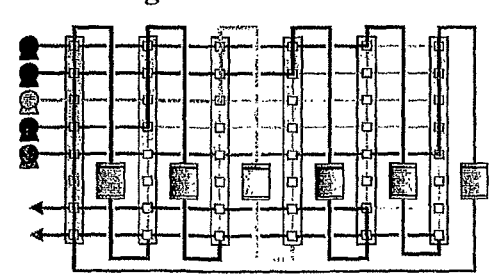
Figure 16:
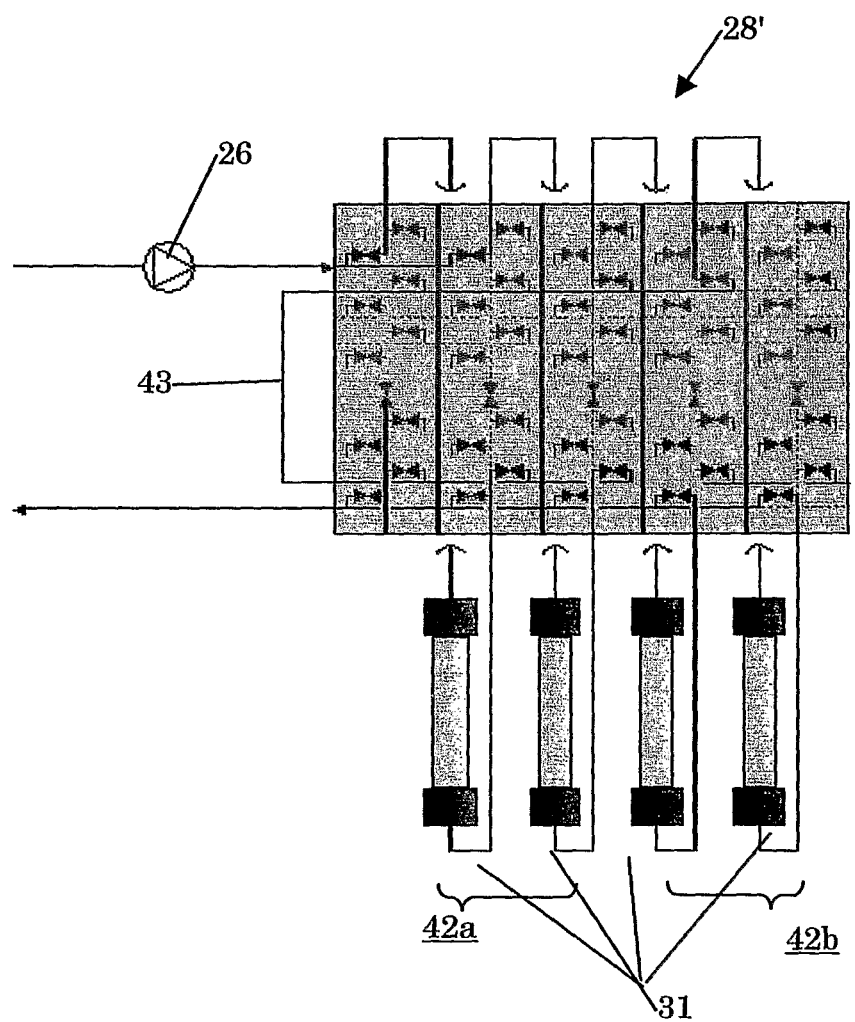
FIG. 16 schematically depicts a system including an adsorber cartridge.

Although FIG. 13 shows a single membrane, typically, a plurality of adsorber cartridges may be interconnected (see also FIG. 14-FIG. 16). The processor is programmed to control the valve arrangement to operate in a countercurrent flow mode in actions 110, 130 and 410 and 430 respectively, as explained with reference to FIG. 1 and FIG. 4.

The switch times are preferably controlled such that the effective membrane transport rate is balanced with the incoming flux of components to be adsorbed. Considering the low volumetric capacities and the low volume of membrane material in the cartridge, the transport rate of the membrane adsorbers should be relatively high and as a consequence, the switch time is relatively short. In a preferred mode, the processor is programmed to provide a cycle rate as a function of a volumetric capacity of the membrane; the effective membrane transport rate and an incoming flux of components to be adsorbed.

Hardware and the control algorithms are preferably provided for providing short loading times, arriving at high cycle rates in view of relatively low volumetric capacity of membrane adsorbers. In this way, a continuous chromatographic purification process can be realized using multiple membrane adsorbers.

In a method for providing biopharmaceutical products involving a Bind & Elute chromatographic separation, the system can be used as shown in FIG. 14 and FIG. 15. In FIG. 15, the different steps of valve switching arrangements of FIG. 14 are depicted, so as to subsequently subject said membrane adsorber cartridges to a number of process steps of a process cycle; to thereby operate in a countercurrent flow mode. The system has Wash input flow 1500, Elute input flow 1501, Clean input flow 1502, Equilibration input flow 1503, and Product Feed in put flow 1504. Furthermore, Output flows Product 1505 and Waste 1506 are provided.

The assembly comprises six membrane adsorber cartridges 31, five pumps 26 and six valve manifolds 1. In this scheme, a first zone 38 is formed by two serially interconnected membrane adsorber cartridges 31. The inlet of the first membrane adsorbers is connected to a feed pump supplying feed solution to the system. The outlet of the second membrane adsorber cartridge in this series is directed to a waste effluent through one valve manifold 1. The second, third, fourth and fifth zone only comprise one single membrane adsorber cartridge 31.

The membrane adsorber cartridge in the second zone is connected to a pump providing an equilibration to the system. The effluent of the membrane adsorber cartridge is directed to the waste outlet. The membrane adsorber cartridge in the third zone is connected to a pump providing a cleaning solution or regenerant to the system. The effluent of the membrane adsorber cartridge is directed to the waste outlet. The membrane adsorber cartridge in the fourth zone is connected to a pump providing an elution buffer to the system. The effluent of the membrane adsorber cartridge is directed to the product outlet. The membrane adsorber cartridge in the fifth zone is connected to a pump providing a wash solution to the system. The effluent of the membrane adsorber cartridge is directed to the product outlet.

As shown in subsequent FIGS. 15a-f, the valve manifolds are organized in such a way that all branch ducts for the system are connected to each other. This may involve pipes or tubing between the valve manifolds, or preferably, by directly interconnecting the valve manifolds. The outlets of the last manifold are closed.

By going though the subsequent steps, each membrane adsorber cartridges is subjected to the series of steps normally involved in Bind & Elute chromatography. The loading is performed in two serially connected membrane adsorber cartridges, thereby allowing the first column to be essentially overloaded. Any product that breaks through will be captured by the next membrane adsorber cartridge. Once the first membrane adsorber cartridge is saturated, it will be subjected to a wash step (step b), followed by the elution step to collect the product (step c). Before being redirected towards the loading step, the membrane adsorber cartridge is subjected to a cleaning process (step d) and equilibration process (step e). The membrane adsorber cartridge is then ready to be used as the last cartridge in the loading zone (step f).

In principle, it is not required to switch all valves at the same time. In one aspect of the invention, the valves can switch asynchronously, thereby controlling the residence time of the membrane adsorber cartridge in each zone individually.

In principle, any zone could comprise more than one membrane adsorber cartridge connected in series by adding additional valve cassettes 1 and membrane adsorber cartridges 31. In a similar way, additional zones can be added by using valve cassettes with an extra inlet port and adding an additional pump 26.

Furthermore, FIG. 16 shows two serially switched sets 42a 42b, each set comprising two parallel cartridges 31. The switching arrangement 28' thus provides a pair of parallel coupled cartridges 31 using the modular valve manifolds 1 according to the invention. In particular, an external loop 43 effectively provides a parallel coupling of the cartridges 31.

Aspects of the invention are paraphrased in the following clauses: use of membrane adsorbers in a multistage chromatography process, comprising multiple membrane adsorbers that are connected in a configuration allowing simultaneously: binding the component of interest in a countercurrent contact mode; washing the saturated membrane adsorbers with a buffer to displace all process fluid from the dead volume in the adsorber cartridges; eluting the product of interest from the membrane adsorbers in a countercurrent contact mode. Preferably additional zones are present in the configuration to clean and/or strip and subsequently equilibrate the membrane adsorbers before they enter the binding zone again. Preferably, such use is combined with a modular disposable format valve cassette and/or combined with disposable components for all wetted materials. For the purification of recombinant protein products preferably affinity chromatography is used; ion exchange chromatography or mixed mode chromatography to bind and elute the product of interest. For the purification of monoclonal antibodies, protein A chromatography, cation exchange or mixed mode ligands to bind and elute the monoclonal antibody of interest is preferably used. For the purification of DNA or viral vectors, affinity chromatography is preferably used and/or ion exchange or mixed mode ligands to bind and elute the DNA or viral vector of interest.

Further aspects comprise use of membrane adsorbers in a multistage chromatography process, comprising multiple membrane adsorbers that are connected in a configuration allowing simultaneously; binding a contaminant or a group of contaminants from the process fluid in a countercurrent contact mode; regenerating the membrane adsorbers in a countercurrent contact mode by contacting them with a process solution or buffer that desorbs the contaminant from the membrane adsorbers. Additional zones in the configuration to wash, clean and/or strip and subsequently equilibrate the membrane adsorbers may be arranged before they enter the binding zone again. This may be used in particular for polishing of monoclonal antibodies, recombinant proteins, viral vectors or DNA products.

Although the invention has been described with reference to the exemplary embodiments, the invention is not limited thereto. For instance, the device can be made of a single constituent piece or several pieces with specific duct structures, which can include all kind of additional branching and valving structures. The invention is not limited to the diaphragm valves of the type disclosed but could incorporate other kinds of valves with adequate functional characteristics. These and other modifications are deemed to fall within the scope of the invention, as claimed in the annexed claims.

The invention claimed is:

1. A method for providing a biopharmaceutical product involving a chromatographic separation process, the method comprising:
   providing a plurality of membrane adsorber cartridges;
   providing a plurality of valves, communicatively coupled to said plurality of membrane adsorber cartridges, at least some of the cartridges being connected in series; and
   switching the valves, so as to subsequently subject said membrane adsorber cartridges to a number of process steps of a process cycle; to thereby operate in a countercurrent flow mode;
   performing a binding action including providing a process fluid in at least one of said plurality of membrane adsorber cartridges for binding a component of interest to a membrane adsorber provided in said at least one membrane adsorber cartridge; and
   performing an eluting action including providing an elution fluid flow in said at least one adsorber cartridge to elute a product of interest from the at least one membrane adsorber; and
   providing the product of interest as the biopharmaceutical product; wherein
   a first switching action including switching at least one first valve of the valve assembly initiates the elution action; and wherein
   a second switching action including switching at least one second valve of the valve assembly initiates said binding action; and wherein
   the first valve and the second valve are switched asynchronously, thereby controlling the residence time of the membrane adsorber cartridge in each zone individually, and
   wherein said eluting action further includes:
   a washing action including providing a buffer in said membrane adsorber cartridge to displace said process fluid from a dead volume in said at least one membrane adsorber cartridge by said buffer; followed by
   a fourth switching action including switching at least one valve of the valve assembly to initiate providing said elution fluid flow to elute the product of interest.

2. A method according to claim 1, wherein said binding action further includes;
- a regenerating action including providing at least one regenerating fluid in said at least one adsorber cartridge to the membrane adsorbers; followed by
- a third switching action including switching at least one valve of the valve assembly to initiate said providing of said process fluid for binding a component of interest.

3. A method according to claim 2 wherein said at least one regenerating fluid has functionality to clean, sanitize and/or strip and/or equilibrate the membrane adsorbers prior to binding the component of interest.

4. A method according to claim 1, wherein said plurality of valves is combined in at least one modular disposable format valve cassette.

5. A method according to claim 1, wherein said membrane adsorber cartridge has adsorber functionality using affinity chromatography, ion exchange chromatography and/or mixed mode chromatography to bind and elute a product of interest.

6. The method according to claim 5 wherein the steps are performed to purify recombinant protein products.

7. A method according to claim 1, wherein said membrane adsorber cartridge has adsorber functionality using protein A chromatography, cation exchange and/or mixed mode ligands.

8. The method according to claim 7 wherein the steps are performed to purify monoclonal antibodies.

9. A method according to claim 1, wherein said membrane adsorber cartridge has adsorber functionality using affinity chromatography, ion exchange or mixed mode ligands.

10. The method according to claim 9 wherein the steps are performed to purify DNA or viral vectors.

11. A method according to claim 1, wherein said process steps include, in an iterative way:
- performing a binding action including providing a process fluid in at least one of said plurality of membrane adsorber cartridges for binding a group of contaminants to a membrane adsorber provided in said at least one membrane adsorber cartridge; and
- performing a regenerating action including providing at least one regenerating fluid in said at least one adsorber cartridge to the membrane adsorbers prior to the binding action, wherein a first switching action including switching at least one valve of the valve assembly initiates said regenerating action; and wherein a second switching action including switching at least one valve of the valve assembly initiates said binding action.

12. A method according to claim 11, wherein at least one regenerating fluid has desorbing functionality to desorb a contaminant from the at least one membrane adsorber.

13. A method according to claim 11 wherein said at least one regenerating fluid has functionality to clean, sanitize and/or strip and/or equilibrate the membrane adsorbers prior to binding the component of interest.

14. The method according to claim 11 wherein the steps are performed to polish monoclonal antibodies, recombinant proteins, viral vectors or DNA products.

15. The method of claim 1 wherein, after initiating the elution action by performing the first action, the second switching action is performed to repeat the binding action until a stopping criterion is reached, and wherein the stopping criterion is taken from the group consisting of: a time period elapses, and a concentration of a specific product is reached.

* * * * *